(12) United States Patent
Keren

(10) Patent No.: US 6,676,608 B1
(45) Date of Patent: Jan. 13, 2004

(54) METHOD AND APPARATUS FOR MONITORING THE CARDIOVASCULAR CONDITION, PARTICULARLY THE DEGREE OF ARTERIOSCLEROSIS IN INDIVIDUALS

(75) Inventor: Hanan Keren, Kfar Saba (IL)

(73) Assignee: Cheetah Medical Ltd., Kfar Saba (IL)

( * ) Notice: Subject to any disclaimer, the term of this patent is extended or adjusted under 35 U.S.C. 154(b) by 0 days.

(21) Appl. No.: 09/577,001

(22) Filed: May 23, 2000

(30) Foreign Application Priority Data

Apr. 19, 2000 (IL) ................................................ 135762
May 11, 2000 (IL) ................................................ 136079

(51) Int. Cl.[7] ................................................ A61B 5/02
(52) U.S. Cl. ...................... 600/481; 600/300; 600/301; 600/500; 600/504
(58) Field of Search ................................ 600/481, 485, 600/483, 490–493, 500–507

(56) References Cited

U.S. PATENT DOCUMENTS

| | | | | |
|---|---|---|---|---|
| 4,425,922 A | * | 1/1984 | Conti et al. ................ | 600/504 |
| 4,807,638 A | * | 2/1989 | Sramek ...................... | 600/485 |
| 4,928,692 A | * | 5/1990 | Goodman et al. .......... | 600/324 |
| 4,960,126 A | * | 10/1990 | Conlon et al. .............. | 600/336 |
| 5,647,369 A | | 7/1997 | Petrucelli et al. | |
| 5,649,543 A | * | 7/1997 | Hosaka et al. .............. | 600/493 |
| 5,671,734 A | | 9/1997 | Pugh | |
| 5,715,826 A | * | 2/1998 | Horrocks et al. ........... | 600/485 |
| 5,752,920 A | * | 5/1998 | Ogura et al. ................ | 600/494 |
| 5,865,755 A | * | 2/1999 | Golub ........................ | 600/485 |
| 6,036,651 A | * | 3/2000 | Inukai et al. ............... | 600/485 |
| 6,120,459 A | * | 9/2000 | Nitzan et al. ............... | 600/493 |
| 6,186,954 B1 | * | 2/2001 | Narimatsu .................. | 600/490 |
| 6,331,162 B1 | * | 12/2001 | Mitchell ..................... | 600/485 |
| 6,355,000 B1 | * | 3/2002 | Ogura ........................ | 600/490 |

FOREIGN PATENT DOCUMENTS

JP                3140007 B2 * 11/2000 ........... A61B/5/022

* cited by examiner

Primary Examiner—Eric F. Winakur
Assistant Examiner—Patricia Mallari
(74) Attorney, Agent, or Firm—G. E. Ehrlich Ltd.

(57) ABSTRACT

A method and apparatus for monitoring the presence of arteriosclerosis in an individual includes detecting an ECG signal of the individual's heart, detecting a blood front wave in a peripheral artery of the individual, and measuring the time lag between a predetermined reference point of the detected blood front wave and a predetermined reference point in the ECG signal to provide an indication of the cardiovascular condition of the individual, particularly arteriosclerosis or arterial obstruction.

25 Claims, 6 Drawing Sheets

METHOD AND APPARATUS FOR MONITORING THE CARDIOVASCULAR CONDITION, PARTICULARLY THE DEGREE OF ARTERIOSCLEROSIS IN INDIVIDUALS

FIELD AND BACKGROUND OF THE INVENTION

The present invention relates to a non-invasive and simplified method and apparatus for monitoring the cardiovascular condition of an individual. The invention is particularly useful for monitoring the degree of arteriosclerosis and/or arterial obstruction in an individual, and is therefore described below with respect to this application.

Arteriosclerosis is a condition in which arteries become thick and hard and loose their supple and elastic quality primarily as a result of aging and the deposit of fats, etc. on the vessel walls. It accounts for a large proportion of heart attacks and ischemic conditions produced by an inadequate blood supply to a region caused by a constriction or obstruction of a blood vessel in the arterial vascular system. It also accounts for many strokes, numerous instances of peripheral vascular disease, and most aneurysms of the aorta, which can rupture and cause fatal hemorrhage.

The loss of elasticity of, and the deposit of fats on the artery walls are believed to be part of the normal aging process. However, arteriosclerosis is more likely to occur, or to increase in severity, in individuals who are overweight, smoke, have high blood pressure, suffer from diabetes, or have a family history of high cholesterol. Many techniques have been devised, both non-invasive and invasive, for monitoring the cardiovascular condition of an individual, and particularly for detecting the degree of arteriosclerosis or arterial obstruction that may be present.

OBJECTS AND BRIEF SUMMARY OF THE INVENTION

An object of the present invention is to provide a novel non-invasive and simplified method and apparatus for monitoring the cardiovascular condition of an individual, which method and apparatus can be implemented in a relatively simple and non-invasive manner. Another object of the invention is to provide a method and apparatus for detecting, and measuring the degree of, arteriosclerosis or arterial obstruction in an individual in a simple and non-invasive manner.

According to one aspect of the present invention, there is provided a method of monitoring the cardiovascular condition of an individual, comprising: detecting an ECG signal of the individual's heart; detecting a blood front wave in a peripheral artery of the individual; and measuring the time lag between a predetermined reference point in the detected blood front wave and a predetermined reference point in the ECG signal such as to provide an indication of the presence of arteriosclerosis in the individual.

The peak of the R-wave in the ECG signal, and the start of the blood front wave, have been found to be particularly good predetermined reference points since both are generally sharply defined.

According to a further feature in the described preferred embodiments of the invention, the blood front wave is detected non-invasively by applying a probe to a body extremity, such as a finger or toe, supplied by the peripheral artery.

This aspect of the invention thus stems from the discovery of the correlation between the cardiovascular condition of an individual and the time lag experienced by the blood front wave in a peripheral artery of the individual from the ECG signal accompanying the individual's heart action. It has been found that in healthy individuals this time lag varies approximately linearly with age, decreasing about 1 ms for each year. Thus, when a finger probe is used in healthy individuals of about 14–22 in age, this time lag was found to be about 220 ms; and in individuals of about 50–55 in age, it was found to be about 180 ms. On the other hand, in individuals in the age group of 50–55 suffering from diabetes and other conditions affecting the cardiovascular system, this time lag was found to be about 140 ms, significantly lower than what would have been expected.

It is believed that this time lag is directly related to the elasticity and degree of obstruction of the walls of the arterial vascular system. As noted above, such elasticity decreases with age because of natural aging and the deposit of plaques, fats, etc. It is believed that walls of high elasticity tend to cushion or damper the blood front wave produced by the heart so as to produce a relatively large time lag from the peak of the detected R-wave to the start of the blood front wave. Accordingly, as the arterial wall is made less elastic by aging and the build-up of deposits, this "cushioning" effect is reduced, thereby reducing this time lag. By thus measuring this time lag, it is believed one can provide a fairly accurate indication of the elasticity of the arterial wall, and thereby the degree of deposit build-up on the individual's arterial walls. If the measured time lag for the particular age of the individual is significantly less than that which would be expected in a healthy individual of the respective age and similar physical build (as indicated above), this would indicate not only the presence of arteriosclerosis, but also the extent of arteriosclerosis in the respective individual.

According to further features in the preferred embodiment of the invention described below, the blood front wave is detected in a body extremity of the individual, particularly in the individual's finger or toe. This makes the test very simple and non-invasive.

According to a still further feature, the blood front wave is detected by an optical oximeter measuring the oxygen saturation of the blood. Such a detector has been found to output an electrical signal closely following the actual blood front wave produced by the heart action accompanied by the ECG signal. The two signals can be displayed on an oscilloscope, to enable an accurate determination to be made of the time lag between the two signals.

According to another aspect of the present invention, there is provided a method of detecting arteriosclerosis in an individual comprising: detecting the blood front wave in a peripheral artery of the individual; examining the shape of the blood front wave; and comparing its shape with a reference corresponding to the shape of the blood front wave in a healthy person to provide an indication of the presence of arteriosclerosis in the individual.

This aspect of the invention stems from the discovery of the correlation between the shape of the blood front wave in a healthy individual with respect to one having arteriosclerosis or obstruction of an artery. Thus, the blood front wave of a healthy individual includes a hump or step arising by the operation of the mitral valve; whereas an individual suffering from arteriosclerosis does not have such a hump or step. The presence of such a hump or step can be easily discerned in a display of the blood front wave on an oscilloscope, or can be easily detected by a spectral density analyzer which determines the ratio of the high-frequency power component ($S_{HF}$) to the low-frequency power component ($S_{LF}$). Thus, in a healthy individual $S_{HF}/S_{LF}$ is generally from 0.05–0.1, so that when this ratio is less than 0.05, this would indicate an arteriosclerosis condition, which would be considered quite severe if there is no hump or step at all in the blood front wave, such that $S_{HF}/S_{LF}$ was equal to zero.

According to a still further aspect of the present invention, there is provided a method of monitoring the cardiovascular condition of an individual, comprising: detecting a first blood front wave in a body part of the individual supplied by a peripheral artery; detecting a second blood front wave in another body part of the individual supplied by a different peripheral artery; and measuring the time lag between predetermined reference points of the first and second blood front waves to provide an indication of the cardiovascular condition of the individual.

For example, in a healthy person, the blood front wave in a toe of the individual lags the blood front wave in a finger of the individual by about 50 ms, increasing a small fraction of a single ms each year of age because of the longer arterial path of a toe as compared to a finger. If this delay is found in an examined individual to be substantially greater than that for a healthy individual of the same age, this would indicate an arteriosclerosis condition particularly in the leg.

This aspect of the invention can thus be used generally to indicate the presence of arteriosclerosis without the need of ECG equipment for detecting the individual's ECG signal. However, more accurate results are obtainable when the ECG signal is also detected and used for determining the lag in the two blood front waves both with respect to the ECG signal and with respect to each other.

According to still further aspects of the present invention, there is provided apparatus for monitoring the cardiovascular condition of an individual in accordance with the above methods.

As described more particularly below, the method and apparatus of the present invention have been found to be particularly useful for monitoring the elasticity of the individual's arterial blood vessel, and thereby the degree of arteriosclerosis that may be present in the individual's arterial vascular system.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
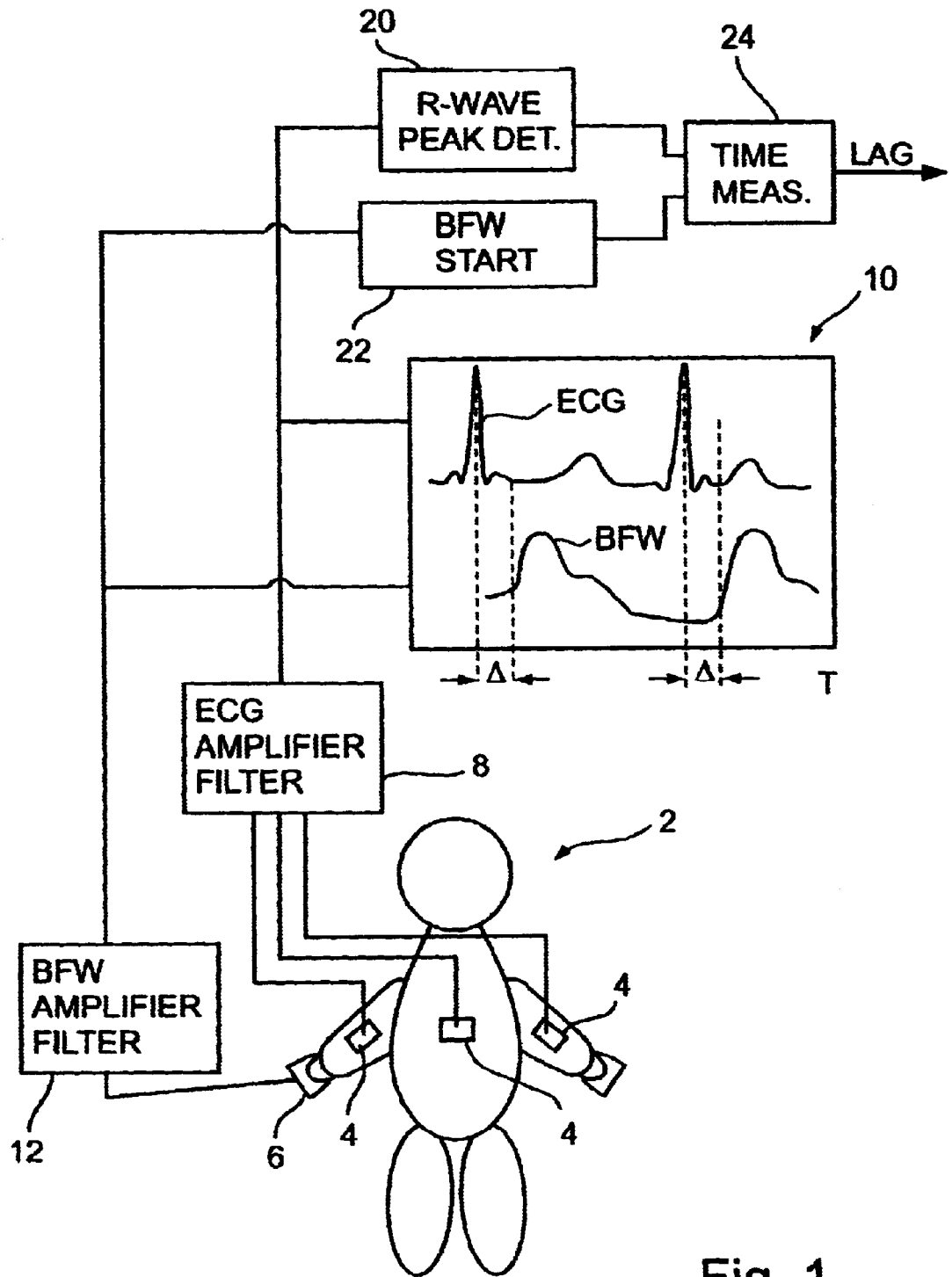
FIG. 1 illustrates one form of apparatus constructed in accordance with the present invention.

FIG. 1 illustrates one form of apparatus constructed in accordance with the present invention for monitoring the cardiovascular condition of an individual 2, and particularly for measuring the degree of arteriosclerosis or arterial obstruction, if any, present in the individual.

For this purpose, the apparatus includes electrocardiogram (ECG) detector electrodes 4 for detected ECG signals accompanying heart activity of the individual. It also includes a blood front wave (BFW) detector 6 for detecting pulsatile volume changes in the arterial vascular system of a body extremity of the individual, in this case the individual's finger. Detector 6 detects, and outputs a BFW signal corresponding to, the pulsatile volume changes in the arterial vascular system of the individual's body extremity, preferably a finger or toe of the individual.

The detected ECG signal is amplified and filtered in a circuit 8, and is displayed in one channel of an oscilloscope 10. The detected BFW signal is amplified and filtered in a circuit 12 and is displayed in a second channel of oscilloscope 10. Thus, both the ECG signal and the BFW signal are concurrently displayed on oscilloscope 10 so that the time relation of the two signals can be viewed and measured to provide an indication of the cardiovascular condition of the individual.

Figure 2:
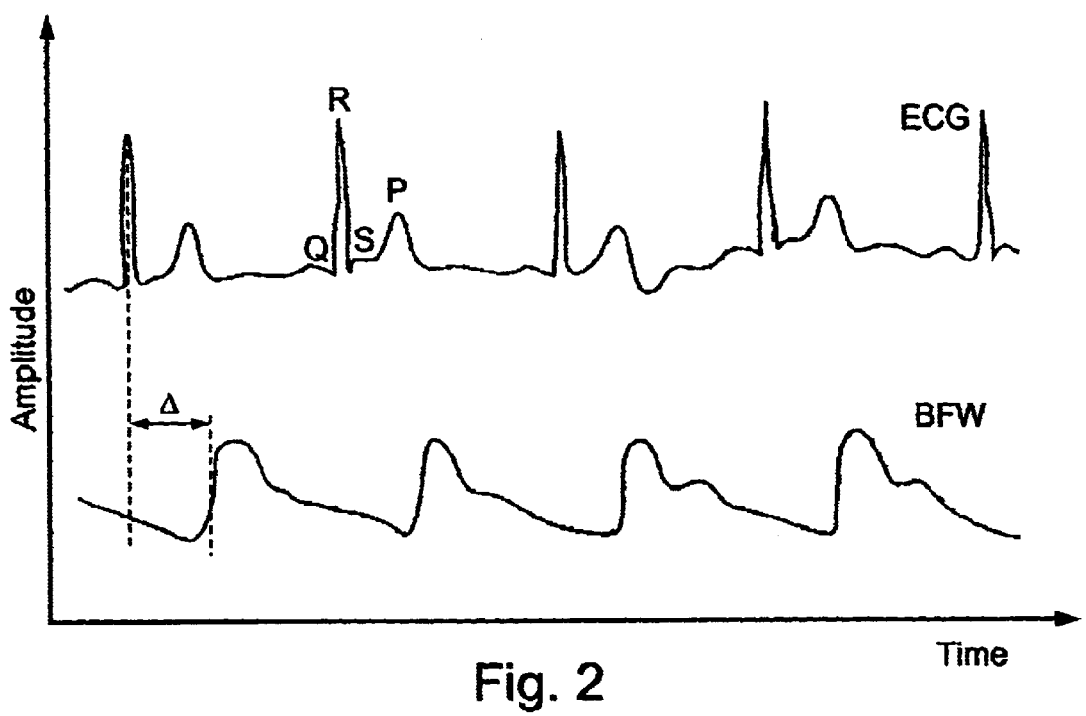
FIG. 2 illustrates an example of the two waveforms produced by the apparatus of FIG. 1, and particularly the manner of measuring the time lag between the detected blood front wave and the detected ECG signal of the individual.

As described earlier, it has been found that the BFW signal, representing the pulsatile blood flow in the arterial vascular system, lags the ECG signal accompanying heart activity in a predetermined manner, depending primarily on age, in healthy individuals. This lag is shown in FIG. 2 as "Δ". Accordingly, any inordinate variation in "Δ" over the predetermined age-dependent value would appear to be primarily due to loss of elasticity, and/or increase in obstruction, in the arterial vascular system of the individual, not dependent primarily on age, and therefore may be used as a basis for generally indicating an arteriosclerosis or obstruction condition, and also the degree of such condition if present.

According to the present invention, a reference point of the ECG signal is compared to a reference point of the BFW signal to determine the lag (Δ) of the BFW signal with respect to the ECG signal. In the preferred embodiment described herein, the two reference points are the peak of the R-wave of the ECG signal, and the start of the BFW signal. As indicated above, this lag in healthy individuals in the age group of 14–22 is approximately 220 ms in the finger, decreasing up to 1 ms for each age, such that healthy individuals in the age group of 50–55 show a lag of approximately 180 ms in the finger. In comparison, individuals suffering from diabetes, or other conditions affecting the cardiovascular system, in the age group of 50–55, show a lag in the finger of about 140 ms, thereby showing that the arterial vascular system of such individuals is less elastic or inordinately obstructed, indicating an arteriosclerosis condition.

The ECG detector 4 and ECG signal processor 8 in FIG. 1 may be one of those used in existing ECG apparatus.

Detector 6 for producing the BFW signal is preferably in the form of a finger probe containing an infrared-type oximeter measuring the oxygen saturation of the blood, such as are known for measuring pulse rate and plethysmographic pulse waves. The finger sensor probe supplied by BCI International, model 3044, has been found particularly useful for this purpose.

Figure 3:
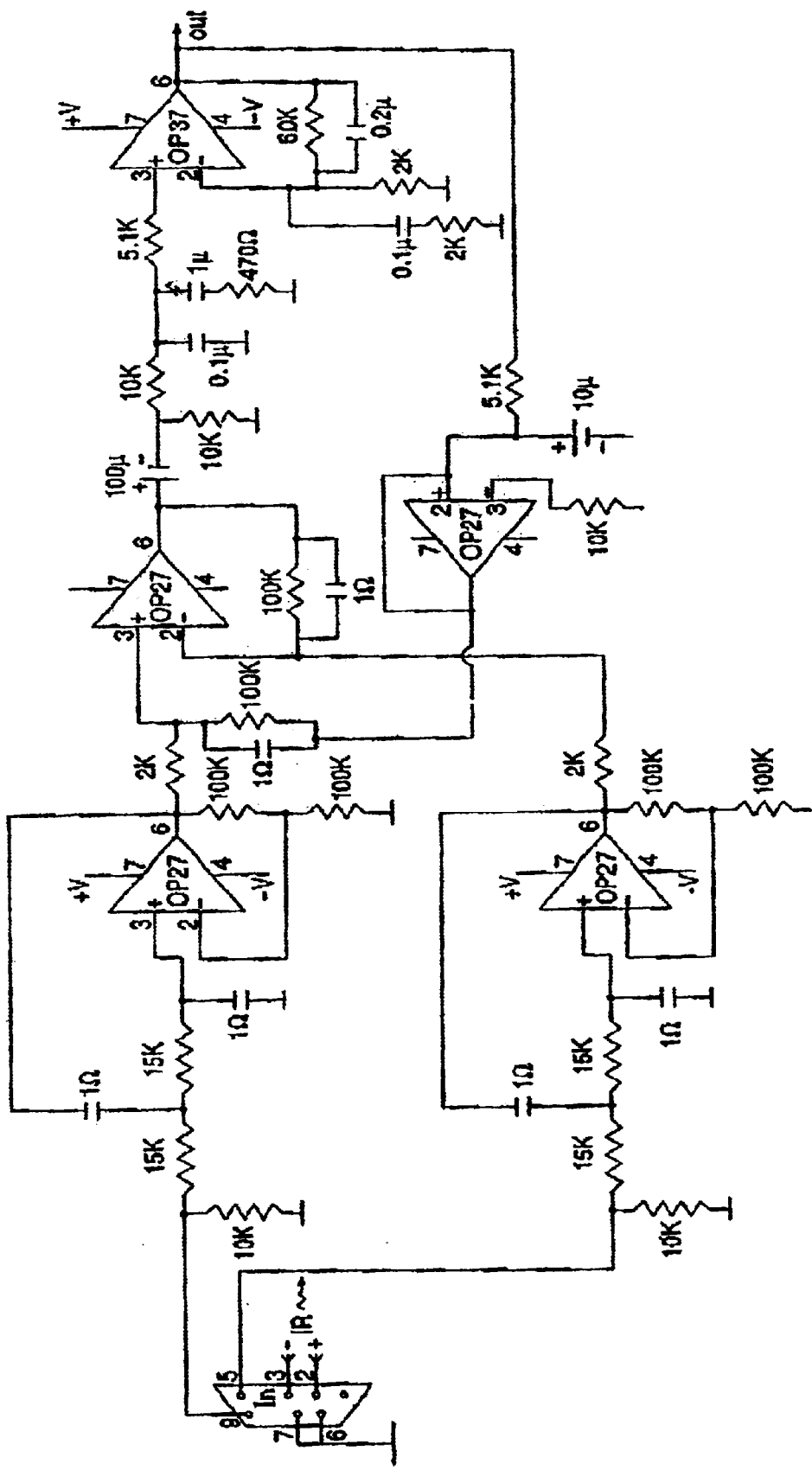
FIG. 3 illustrates an example of an electrical circuit which may be used with an optical oximeter type detector for producing the blood front wave signal of the individual by measuring the oxygen saturation of the blood.
Figure 4:
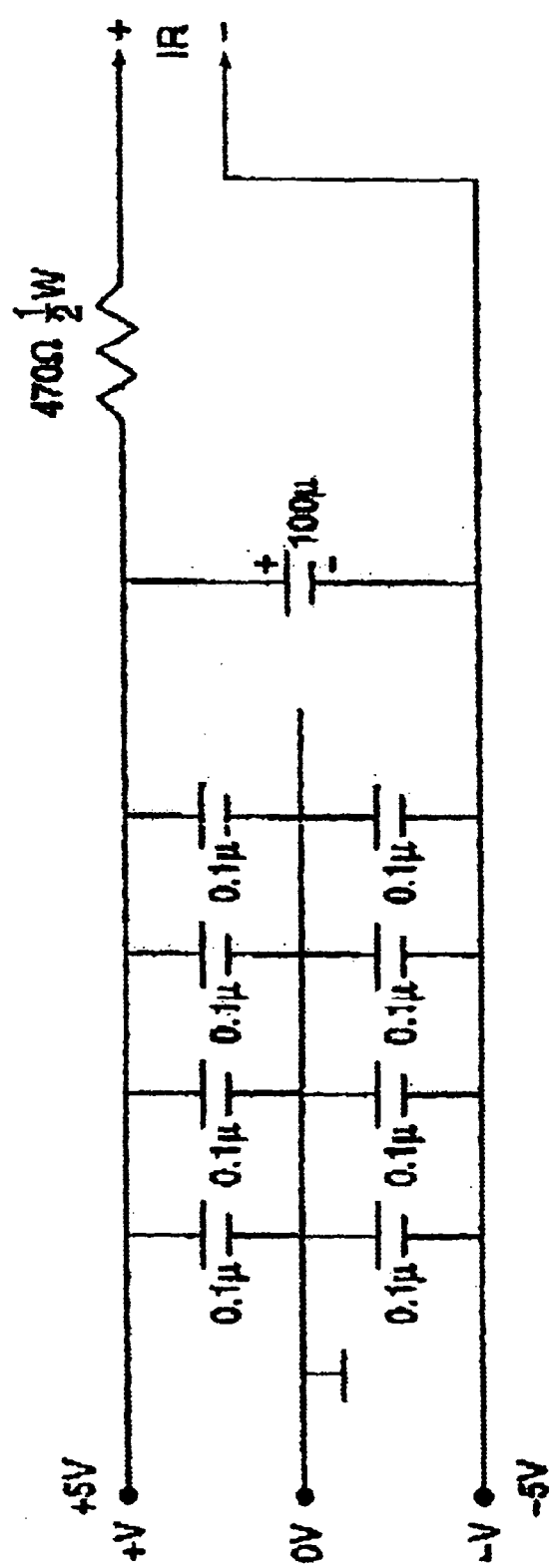
FIG. 4 illustrates an electrical circuit which may be used as the oximeter driver in the circuit of FIG. 3.

FIG. 3 illustrates a preferred circuit which may be used as the BFW signal processor 12 for filtering and amplifying the signal outputted by detector 6; and FIG. 4 illustrates a preferred driver circuit for the infrared source in the oximeter detector 6.

As indicated earlier, the oscilloscope 10 receives the ECG and BFW signals on separate channels and thereby permits the time relationship between the two signals to be visually compared and measured.

FIG. 1 illustrates additional circuitry that may be provided for electrically measuring the time lag between the ECG and BFW signals.

Thus, the peak of the R-wave in the ECG signal is detected by circuit 20; and the start of the BFW signal is detected by circuit 22. The time lag between the start of the detected BFW signal, and the peak of the detected R-wave of the ECG signal, is measured in a time measuring device 24, which produces an output of this time difference, i.e., the lag between the start of the BFW signal and the peak of the R-wave in the ECG signal. As indicated earlier, this lag is compared to the known age-dependent lag for healthy individuals, to thereby provide an indication of the presence, and degree, of arteriosclerosis in the individual examined.

Figure 5:
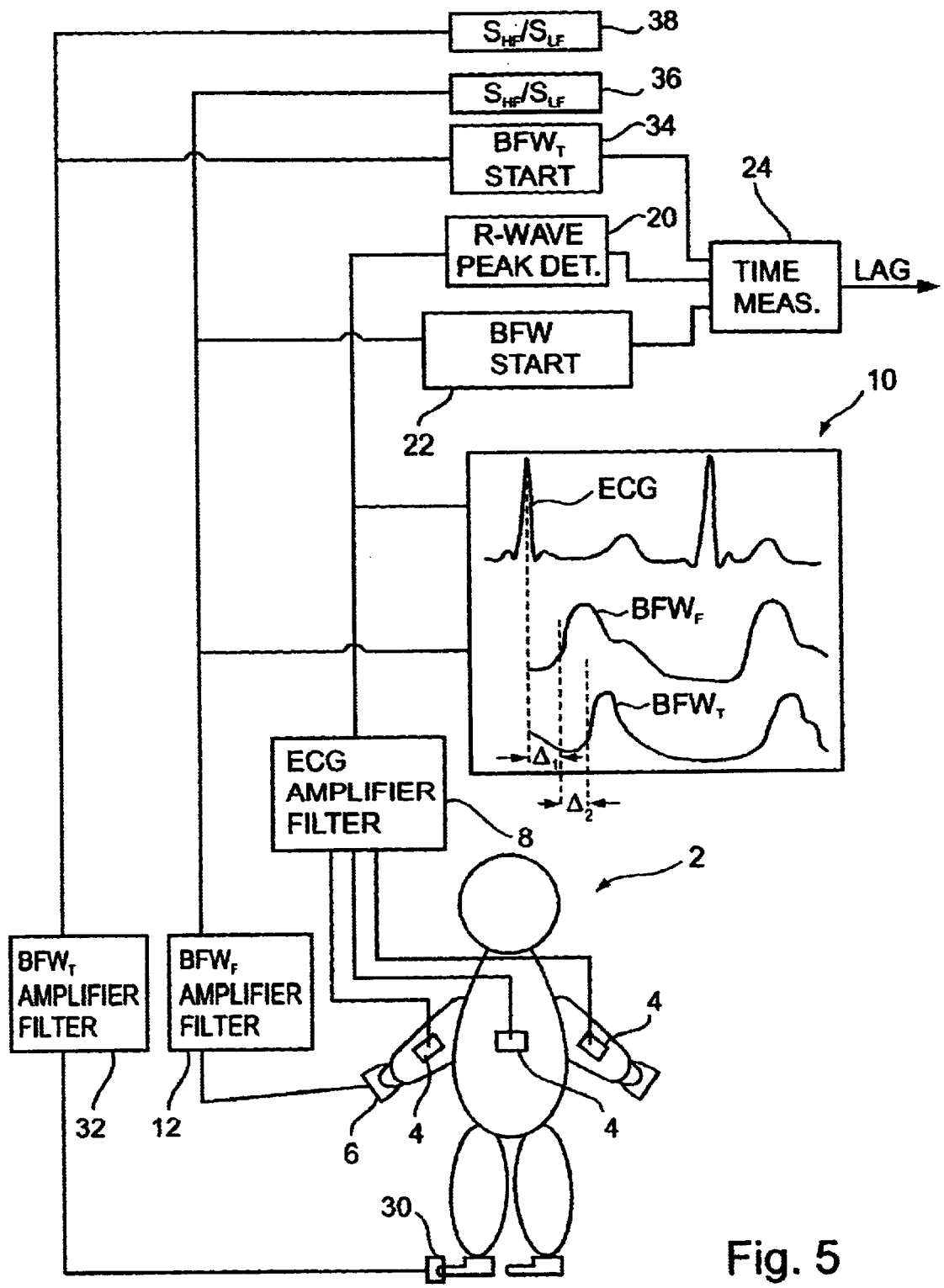
FIG. 5 illustrates another form of apparatus constructed in accordance with the present invention for analyzing the shape of the blood front wave signal, and also for producing two such signals from two different body parts (finger and toe) of the individual.

FIG. 5 illustrates another apparatus, similar to that of FIG. 1, except that it detects, and displays on oscilloscope 10, the blood front waves from two parts of the individual's body (in this case, the finger and toe) supplied by different arteries; and in addition, it analyzes both of the detected blood front waves to permit their shapes to be compared with those of healthy individuals. Both of the foregoing additional features provide a better indication of the cardiovascular condition of the individual, particularly the presence of arteriosclerosis and/or obstruction in an artery.

Those parts of the apparatus illustrated in FIG. 5 which are common to those included in the apparatus of FIG. 1 are identified by the same reference numerals, to facilitate understanding.

Thus, the apparatus illustrated in FIG. 5 includes a second blood front wave (BFW) detector 30, in this case a toe probe, for detecting pulsatile volume changes in the arterial vascular system of the individual's toe. The toe probe 30 thus also outputs a BFW signal, which amplified and filtered in circuit 32, and is displayed in a third channel (the bottom most one in FIG. 5) of oscilloscope 10. The start of the BFW signal produced by the toe probe 30 is detected by a circuit 34; and the time lag between its start, and the peak of the detected R-wave of the ECG signal, is measured in the time measuring circuit 24. Circuit 24 produces outputs representing the lag between the start of each BFW signal and the peak of the R-wave in the ECG signal.

Figure 6:
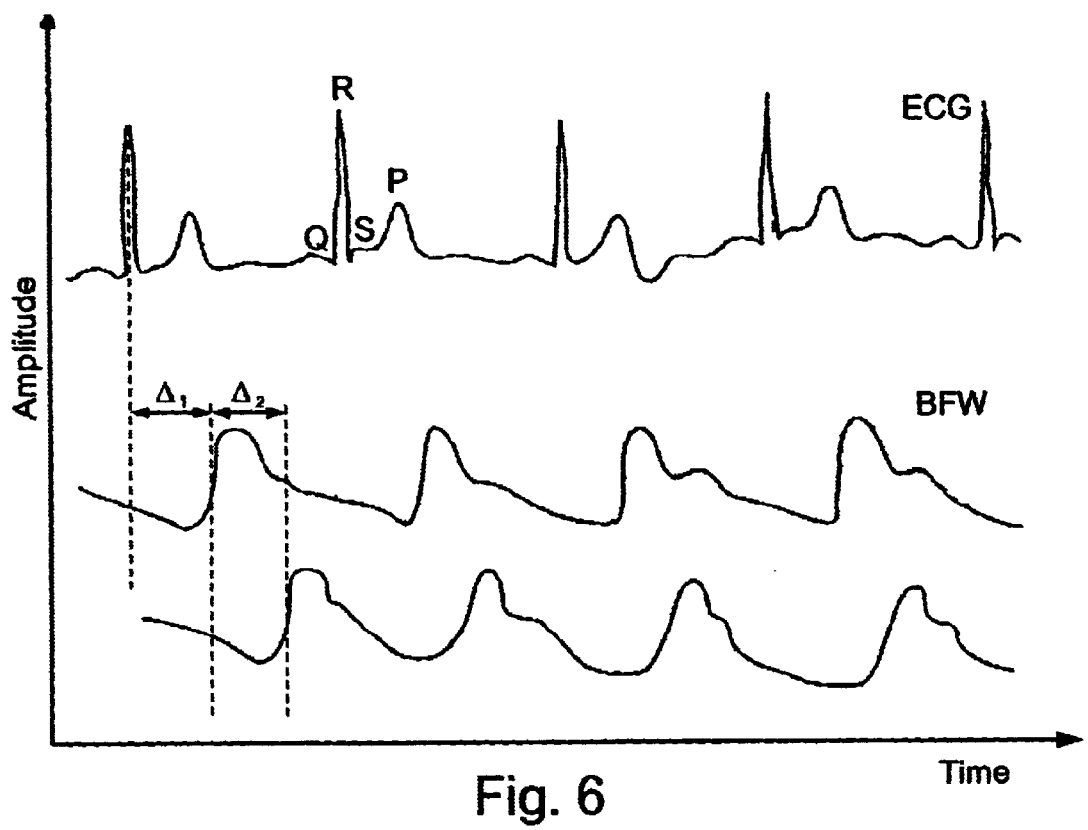
FIG. 6 illustrates examples of three wave forms produced by the apparatus of FIG. 5.

Thus, as shown in FIGS. 5 and 6, the lag between the R-wave peak in the ECG signal and the BFW signal from the finger ($BFW_F$) is indicated by "$\Delta_1$" whereas the lag between the start of signal $BFW_F$ and the BFW signal from the toe probe 30 ($BFW_T$) is indicated as "$\Delta_2$".

As indicated earlier, in a normal healthy person there is approximately a 50 ms lag between $\Delta_1$ and $\Delta_2$, which lag increases by a fraction of a ms for each year of age, corresponding to the increased arterial path to the toe with respect to the finger. If $\Delta_2$ is inordinately larger than what would be expected in a healthy individual, this indicates an arteriosclerosis or obstructive condition in a leg artery.

It will thus be seen that the three displays on the oscilloscope 10, as shown in FIGS. 5 and 6, will provide a reasonably good indication of whether arteriosclerosis or arterial obstruction exists in the individual, and if so, the location thereof particularly if it is in the individual's leg.

As also indicated earlier, the shape of the BFW signals displayed on the oscilloscope 10 will also provide, by themselves, and indication of the cardiovascular condition of the individual. Thus, as shown particularly in FIG. 6, the BFW signal rapidly rises from its start S to its peak P, and gradually declines to the start of the next signal, but in this decline there is a hump H. This hump or step H is due to the operation of the mitral valve. In a healthy individual, this hump H is quite apparent and visually discernable on the oscilloscope; whereas in a patient suffering from arteriosclerosis, this hump substantially or completely disappears, which is also visually discernable on the oscilloscope. Accordingly, if the BFW signal from either the finger probe 6 or toe probe 30 does not include this hump H, this would indicate an arteriosclerosis condition.

Figures 7, 8:
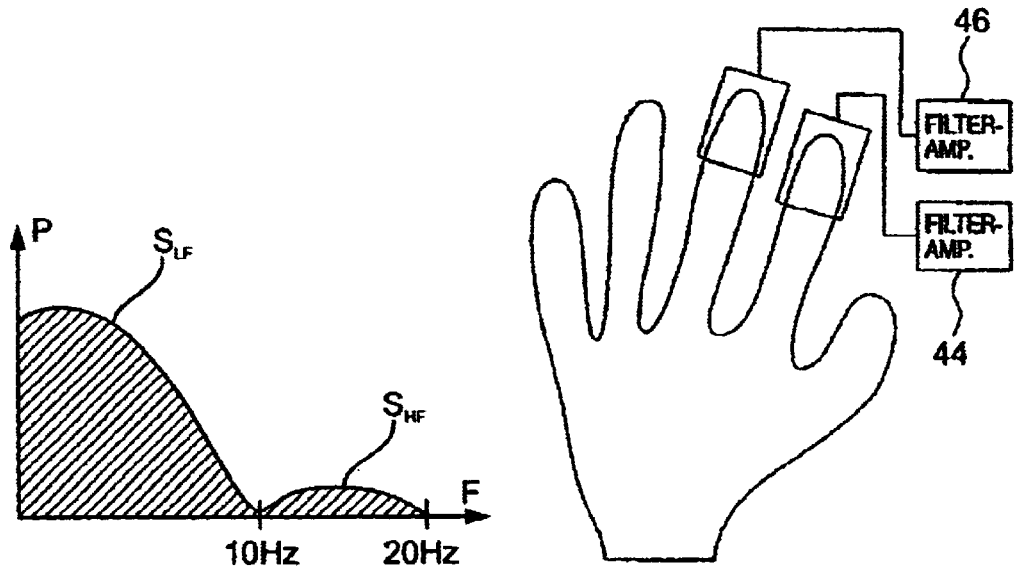
FIG. 7 is a diagram helpful in explaining the manner of using the shape of the blood front wave to provide an indication of the presence of arteriosclerosis.
FIG. 8 illustrates a modification in the apparatus of FIG. 5, wherein the blood front wave is detected in two fingers of the individual, each supplied by a different artery, rather than in a finger and toe of the individual.

FIG. 5 includes an analyzer 36, 38 for analyzing the power spectral density of each of the BFW signals in order to determine electrically whether such a hump or step exists. FIG. 7 illustrates such an analysis in a healthy individual, wherein it will be seen that the signal includes a large low-frequency power component ($S_{LF}$) and a much smaller, but significant, high-frequency power component ($S_{HF}$). In a healthy individual, the ratio $S_{HF}/S_{LF}$ is equal to about 0.05–0.1; whereas in a person suffering from arteriosclerosis, this ratio approaches or is equal to zero. Thus, if this ratio is less than 0.05, this would indicate an arteriosclerosis condition.

It will thus be seen that merely detecting the BFW signals from two body parts supplied by peripheral arteries (e.g., a finger and toe) as illustrated in FIGS. 5 and 6, or merely examining a BFW signal for the presence of the hump or step as described above with respect to FIGS. 6 and 7, can be used (even without detecting the individual's ECG signal) to provide an indication of an arteriosclerosis condition. All three techniques may be used together to provide a more reliable indication of the presence or absence of that condition.

It will be appreciated that if two BFW signals are to be used, they need not to be from the finger and toe of the individual, but could be, for example, from two different fingers supplied by different arteries, or from two different toes supplied by different arteries. The former is schematically indicated in FIG. 8 wherein one finger probe 40 is provided on the individual index finger, and a second probe 42 is provided on the next adjacent finger, since that finger is supplied by a different artery. The BFW signal outputted by probe 40 is amplified and filtered in circuit 44; and the BFW signal outputted by probe 42 is amplified and filtered in circuit 46.

While the invention has been described with respect to several preferred embodiments, it will be appreciated that these are set forth merely for purposes of example, and that many variations may be made. For example, other techniques may be used for measuring the pulsatile volume changes in the arterial vascular system of the finger, toe, ear lobe or other body extremity of the individual being examined to produce the blood front wave (BFW) signal, such as by the use of pressure cuffs, or ultrasound detectors. In addition, other predetermined reference points may be used to measure the time lag between the ECG and BFW signals.

Many other variations, modifications and applications of the invention will be apparent.

What is claimed is:

1. A method of monitoring the cardiovascular condition of an individual to determine the presence of arteriosclerosis in the individual, comprising:

detecting an ECG signal of the individual's heart;

detecting a blood front wave in a peripheral artery of the individual;

measuring the time lag between the start of said detected blood front wave and the peak of the R-wave in the ECG signal;

examining the shape of said blood front wave by analyzing its power spectral density to determine the ratio of the high-frequency power component $S_{HF}$ to the low frequency power components ($S_{LS}$);

and comparing said shape of the blood front wave with a reference corresponding to the shape of the blood front wave in a healthy person to provide, from the measured time lag and the comparison of said shapes, an indication of the presence of arteriosclerosis in the individual.

2. The method according to claim 1, wherein said time lag is measured by concurrently displaying both the detected ECG signal and said detected blood front wave to enable said time lag to be visually measured.

3. The method according to claim 1, wherein said blood front wave is detected non-invasively by applying a probe to a body extremity supplied by said peripheral artery.

4. The method according to claim 3, wherein said probe is applied to a finger or toe of the individual.

5. The method according to claim 3, wherein said probe is an optical oximeter measuring the oxygen saturation of the blood.

6. A method of detecting arteriosclerosis in an individual comprising:

detecting the blood front wave in a peripheral artery of the individual;

examining the shape of the blood front wave by analyzing its power spectral density to determine the ratio of the high-frequency power component ($S_{HF}$) to the low frequency power component ($S_{LF}$);

and comparing its shape with a reference corresponding to the shape of the blood front wave in a healthy person to provide an indication of the presence of arteriosclerosis in the individual.

7. The method according to claim 6, wherein the blood front wave in a peripheral artery is detected by applying a probe to an external part of the body supplied by the peripheral artery.

8. Apparatus for detecting arteriosclerosis in an individual comprising:

a probe attachable to an external body part of an individual supplied by a peripheral artery;

and a display system for displaying the blood front wave to enable its shape to be examined and compared with a reference corresponding to the shape of the blood front wave in a healthy person, to provide an indication of the presence of arteriosclerosis in the individual; and a special density analyzer for determining and displaying the ratio of the high frequency power component ($S_{HF}$) to the low frequency power component ($S_{LF}$) of the blood front wave.

9. The apparatus according to claim 8, wherein said probe is a finger probe or a toe probe.

10. A method of monitoring the cardiovascular condition of an individual to determine the presence of arteriosclerosis in the individual, comprising:

detecting an ECG signal of the individual's heart;

detecting a blood front wave in each of at least two different peripheral arteries supplying blood to different body parts of the individual; and measuring the time lag between the start of each of said detected blood front waves with respect to each other and with respect to the peak in the R-wave in the ECG signal, to provide an indication of the existence of arteriosclerosis or an arterial obstruction in at least one of said body parts, and the location thereof.

11. The method according to claim 10, wherein the two body parts are a finger and a toe of the individual.

12. The method according to claim 10, wherein the two body parts are different fingers or different toes of the individual supplied by different peripheral arteries.

13. A method of monitoring the cardiovascular condition of an individual, comprising:

detecting a first blood front wave in a body part of the individual supplied by a peripheral artery;

detecting a second blood front wave in another body part of the individual supplied by a different peripheral artery;

measuring the time lag between predetermined reference points of said first and second blood front waves, measuring the power spectral density of at least one of said blood front waves to determine the ratio of the high-frequency power component ($S_{HF}$) to the low-frequency power component ($S_{LF}$);

and utilizing said measured time lag and power spectral density to provide an indication of the cardiovascular condition of the individual.

14. The method according to claim 13, wherein each of said probes is an optical oximeter measuring the oxygen saturation of the blood.

15. The method according to claim 13, wherein an ECG signal of the individual's heart is also detected, and the time lag between a predetermined reference point of the ECG signal, and a predetermined reference point of each of said blood front waves, is measured to provide an indication of the cardiovascular condition of the individual.

16. The method according to claim 15, wherein said predetermined reference point of the ECG signal is the peak of the R-wave therein.

17. The method according to claim 13, wherein said predetermined reference point is the start of the respective blood front wave.

18. The method according to claim 13, wherein said blood front waves are detected non-invasively by probes applied to different body extremities of the individual supplied by different peripheral arteries.

19. The method according to claim 13, wherein one of said probes is applied to a finger or a toe of the individual, and the other of said probes is applied to another finger or another toe of the individual.

20. Apparatus for monitoring the cardiovascular condition of an individual to determine the presence of arteriosclerosis in the individual, comprising:

an ECG detector for detecting the ECG signal of the individual's heart, including the R-wave thereof;

two probes constructed and dimensioned so as to be attachable to two different body parts of the individual supplied by different peripheral arteries for detecting the blood front wave in each of the two body parts of the individual;

and a measuring system for measuring the time lag between a predetermined reference point of each blood front wave and the predetermined reference point of the ECG signal such as to provide an indication of the presence of arteriosclerosis in the individual.

21. The apparatus according to claim 20, wherein each of said probes is an optical oximeter measuring the oxygen saturation of the blood in said body extremity.

22. The apparatus according to claim 20, wherein said measuring system includes an oscilloscope for concurrently displaying the ECG signal and the blood front wave signals of the individual.

23. The apparatus according to claim 20, wherein said apparatus further includes a spectral density analyzer for determining the ratio of the high frequency power component ($S_{HF}$) to the low frequency power component ($S_{LF}$), or $S_{HF}/S_{LF}$, of at least one of the blood front waves.

24. The apparatus according to claim 20, wherein one of said probes is a finger probe, and the other of said probes is a toe probe.

25. The apparatus according to claim 20, wherein both of said probes are finger probes or toe probes attachable to different fingers or toes of the individual.

* * * * *

UNITED STATES PATENT AND TRADEMARK OFFICE
CERTIFICATE OF CORRECTION

PATENT NO. : 6,676,608 B1
DATED : January 13, 2004
INVENTOR(S) : Hanan Keren

It is certified that error appears in the above-identified patent and that said Letters Patent is hereby corrected as shown below:

<u>Title page,</u>
Change "[73] Assignee: Cheetah Medical Ltd., Kfar Saba (IL)" to -- [73] Assignee: Cheetah Medical Inc., Wilmington, Delaware --

Signed and Sealed this

Sixth Day of April, 2004

JON W. DUDAS
*Acting Director of the United States Patent and Trademark Office*